United States Patent
Neuberger

(10) Patent No.: US 6,561,808 B2
(45) Date of Patent: May 13, 2003

(54) METHOD AND TOOLS FOR ORAL HYGIENE

(75) Inventor: Wolfgang Neuberger, Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/965,418

(22) Filed: Sep. 27, 2001

(65) Prior Publication Data
US 2003/0059738 A1 Mar. 27, 2003

(51) Int. Cl.$^7$ .............................. A61C 5/00; A61K 7/16
(52) U.S. Cl. .................. 433/215; 433/29; 424/49; 424/58
(58) Field of Search ..................... 433/29, 215, 216; 424/49, 58

(56) References Cited

U.S. PATENT DOCUMENTS

| | | |
|---|---|---|
| 5,611,793 A | 3/1997 | Wilson et al. |
| 5,622,501 A * | 4/1997 | Levy ........................ 433/215 |
| 5,658,148 A | 8/1997 | Neuberger et al. |
| 5,766,011 A | 6/1998 | Sibner |
| 5,863,202 A | 1/1999 | Fontenot et al. |
| 6,001,882 A | 12/1999 | Fox et al. |
| 6,036,493 A * | 3/2000 | Sharma ...................... 433/215 |
| 6,056,548 A | 5/2000 | Neuberger et al. |
| 6,116,900 A | 9/2000 | Ostler |
| 6,251,127 B1 * | 6/2001 | Biel ............................ 607/88 |
| 6,251,419 B1 | 6/2001 | Graber et al. |
| 6,254,388 B1 | 7/2001 | Yarborough |
| 6,254,856 B1 | 7/2001 | Tsuchiya |
| 6,262,030 B1 | 7/2001 | Wu et al. |
| 6,287,120 B1 * | 9/2001 | Wiesel ....................... 433/215 |
| 6,290,496 B1 * | 9/2001 | Azar et al. .................... 433/29 |
| 6,325,623 B1 * | 12/2001 | Melnyk et al. ............... 433/29 |

FOREIGN PATENT DOCUMENTS

| | | | |
|---|---|---|---|
| DE | 33 02 694 A1 | * | 2/1984 |
| DE | 199 50 933 A1 | * | 4/2001 |

* cited by examiner

Primary Examiner—Ralph A. Lewis
(74) Attorney, Agent, or Firm—Bolesh J. Skutnik; B J Associates

(57) ABSTRACT

A method and material for self-cleaning of the teeth and mouth using a source of light in the visible range in conjunction with a photosensitive oral hygiene composition possessing a broad absorption spectrum in the visible range. The invention selectively eliminates harmful bacteria by use of a photosensitive agent and a light source. The present invention involves the use of a light-providing dental device to activate a photosensitive agent and destroy harmful bacteria in the oral cavity. It prevents or deters oral diseases, inflammations, and infections.

5 Claims, 2 Drawing Sheets

METHOD AND TOOLS FOR ORAL HYGIENE

BACKGROUND OF THE INVENTION

1. Field of the Invention

The invention relates generally to a method for at-home tooth- and mouth-cleansing using a light-providing instrument and an oral cleaning rinse containing a photosensitive agent and a material for protection against the derogatory effects of fluids and the oral cavity and to eliminate harmful bacteria in the oral cavity.

2. Information Disclosure Statement

Generally, the prior art uses a method of light-assisted dental treatment that requires professional care and which is performed only in response to specific problems with the oral cavity, i.e. lesions, wounds, microbes, or periodontal disease. Further, the use of lasers at wavelengths less than 1500 nm creates potential hazards, for which safety precautions must be taken to protect the user. Those devices that allow for at-home self care provide for the use of lasers at lower power levels, potentially reducing the effectiveness of the cleaning process.

In addition, previous methods of light-assisted dental treatment do not provide a basic protective material to allow a photosensitizer to attach to bacteria in the oral cavity. In the prior art, photosensitizers suffer from significant degradation in effectiveness from exposure to saliva, white blood cells, and other natural defenses in the mouth. While a photosensitizer readily attaches to bacteria in a media free from these bodily defense mechanisms or other safe media, there are no proven methods that allow for effective protection of a photosensitizer from other substances located within the mouth.

Inflammatory periodontal diseases are among the most prevalent diseases among humans, and the advanced form, chronic periodontitis, is the major cause of tooth loss in adults. Methods of treating chronic periodontitis involve mechanical removal of sub-gingival plaque to eliminate the causative organisms supplemented by anti-microbial therapy. This often involves the use of blunt tools to scrape or otherwise use physical force to remove the plaque. In this manner, removal of plaque is never fully successful. There are disadvantages in the long-term use of the anti-microbial agents included in the therapy; notably, the development of resistance to the agents, rendering them clinically ineffective; and difficulties arising from disturbance of the oral microflora. Further, the development of a prophylactic cleansing method that prevents the buildup of plaque would keep periodontal diseases from setting in.

A prior patent by the inventor (Neuberger, U.S. Pat. No. 5,658,148) describes a laser toothbrush that is available for home treatment but only with use of a laser at a specified wavelength matched to a specified photosensitive agent. A restricted absorption spectrum reduces the effectiveness of alternative light sources to activate a photosensitive agent. These safety restrictions reduce the success of this device for home use.

Another patent by the inventor (Neuberger; U.S. Pat. No. 6,056,548) describes Photodynamic Therapy (PDT) with an enhanced photosensitive agent that again requires a light source at a specified wavelength to activate the photosensitive agent in the oral hygiene composition. In addition, the prior invention does not have any mechanisms for targeting and selecting out only harmful bacteria.

U.S. Pat. No. 5,611,793 (Wilson and Harvey) describes a method of PDT that is for sterilizing wounds or lesions in the oral cavity, designed primarily for use in an office or other medical setting, by a professional in the medical field.

Generally, the present invention provides a method for self-dental care with a light-providing dental device and a toothpaste, mouthwash, rinse, or gel that contains a photosensitive agent with a broad absorption spectrum and is safe for at-home oral use.

OBJECTIVES AND BRIEF SUMMARY OF THE INVENTION

It is an aim of the present invention to address the need for a general hygienic oral cleaning method that has a significant destructive effect on bacteria, viruses, and other microbes, while being generally safe for self-treatment. An oral cleaning method is designed for treatment of any and all tissues, bacteria, or other substances in the oral cavity, including but not limited to the teeth, plaque, tongue, inner cheek tissue, gums, subginivival plaque, food or other residues, palate, and salivary glands.

It is a further aim of the present invention to provide a dental toothpaste, mouthwash, rinse, or gel, generally described as an oral hygiene composition, containing a photosensitive agent, to use in increasing the positive effects of the treatment.

It is another aim of the present invention to provide a photosensitive agent with a wide absorption spectrum.

It is still a further aim of the present invention to provide a substance in the oral hygiene composition that promotes adherence to the teeth and plaque and to insure the photosensitive agent from the derogatory effects of bloods serum, saliva, and other materials located naturally within the oral cavity to allow effective photoactivation.

It is another aim of the present invention to provide a targeting ingredient to allow the oral hygiene composition to discriminate between harmful and benign microbes and thus positively alter the microbial balance of the oral cavity.

It is yet another aim of the present invention to provide a dental device to permit the delivery of light that activates the photosensitive agent and facilitates the elimination of harmful microbes in the oral cavity.

Briefly stated, the invention provides a method and material for self-cleaning of the teeth and mouth using a source of light in the visible range in conjunction with a photosensitive oral hygiene composition possessing a broad absorption spectrum in the visible range. The invention selectively eliminates harmful bacteria by use of a photosensitive agent and a light source. The present invention involves the use of a light-providing dental device to activate a photosensitive agent and destroy harmful bacteria in the oral cavity. It prevents or deters oral diseases, inflammations, and infections.

The above, and other objects, features, and advantages of the present invention will become apparent from the following description read in conjunction with the accompanying drawings.

DETAILED DESCRIPTION OF PREFERRED EMBODIMENTS

In the prior art, summarized earlier, most applications of PDT require a light source of specific wavelength in order to be effective in activating the photosensitive agent. The photosensitive agents involved in prior inventions require a specific wavelength for activation, particularly in the visible region.

In addition, the prior art does not seriously contemplate use and operation by consumers. The present invention addresses a need for prophylactic cleaning rather than treatment. Prior inventions address the treatment of existing dental problems or oral lesions—problems normally addressed by trained medical professionals.

The prior art generally proves the effectiveness of photosensitive agents in adhering to plaque in an environment free from any substance with derogatory effects. However, the prior art generally fails to provide a mechanism or basic dental material or substance for protecting photoactivated compounds from the decomposing effects of the bodies' natural defenses and other substances. Blood serum and saliva, as well as other substances, deteriorate the ability of a photosensitizer to attach to plaque.

Finally, prior art does not include a targeting mechanism along with the photosensitive agent that positively alters the microbial balance of the oral cavity by selectively targeting harmful bacteria, leaving other less harmful microbes to exist.

Figure 1:
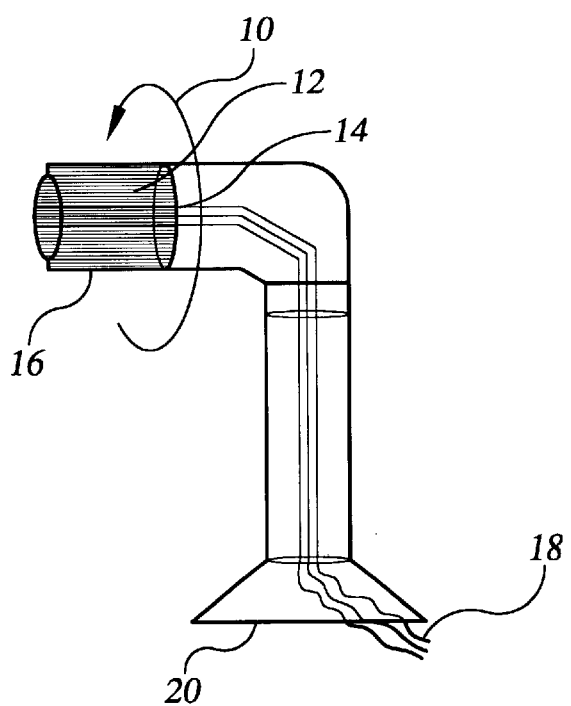
FIG. 1 is a view of the end of the dental device as generally designed in U.S. Pat. No. 5,658,148 (Neuberger).
Figure 4:
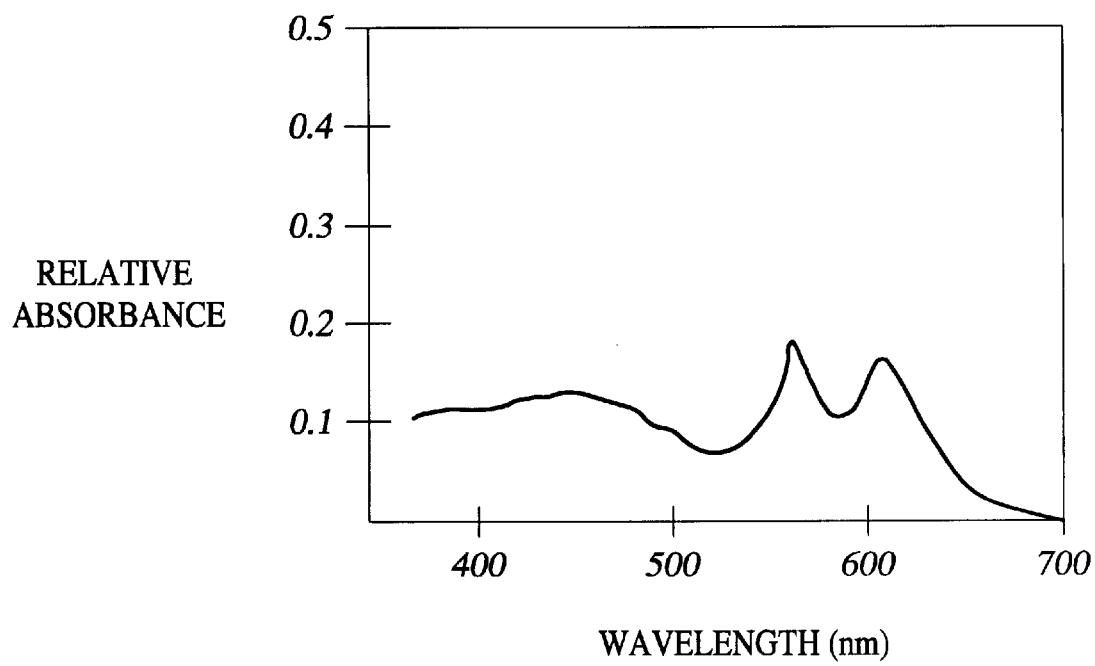
FIG. 4 is a graph of the absorption spectrum of Hypericin, primarily in the visible wavelength region.

In one preferred embodiment, shown in FIG. 1, a dental device similar to the one embodied in U.S. Pat. No. 5,568,148 is employed. A light emitting diode or lamp provides the light source in the dental device in this embodiment. The light source emits from between the bristles or in the middle of the circular structure of the rotating brush head. The oral hygiene composition is applied from the dental device, by use of a conventional toothbrush, or by other means. The use of a low viscosity oral hygiene composition entails intake of a specified dose into the mouth, and moving the composition in the mouth similar to the method one utilizes to use mouthwash. Similarly, an oral hygiene composition with a higher viscosity entails use like one uses conventional toothpastes. The photosensitive agent has a broad absorptive band, as shown in FIG. 4. It is capable of absorbing most, if not all, visible light sources. Hypericin, an extract of Hypericum Perforatum (St. John's Wort), is a suitable photosensitive agent in the preferred embodiment. Lasers at a wavelength of 630 nm are suitable for this embodiment, as are other wavelengths of visible light. The toothbrush contains longer bristles spaced intermittently around the circular head in order to ensure effective cleaning by introduction of the oral hygiene composition as well removal of the photosensitive agent from the inter-dental spaces.

While Hypericin can be extracted in pure form, other extracts of St. John's Wort contain Hypericin as the main chemical with only slight quantities of innocuous impurities. These extracts are also suitable for use with the present invention. The cost of impure Hypericin is also lower than in pure form.

Another possible photosensitive agent suitable for use in the present invention is Erythrosin B. U.S. Pat. No. 6,254,856 (Tsuchiya) describes the use of Erythrosin B in a composition for plaque identification. Erythrosin B is a red substance formed by the oxidation of Tyrosin. It has proved to be a photo-pharmaceutical well suited for use as a photosensitive agent in the present invention.

The oral hygiene composition is well suited for oral use due to elements within the composition that resist the decomposing effects of saliva, blood serum, and other substances occurring naturally in the mouth. An element of the oral hygiene composition protects the photosensitive agent and resists decomposition for sufficient time to allow attachment to teeth and plaque and activation by a light source. The same element, or an additional one, also increases the viscosity of the oral hygiene composition. Increasing viscosity alters the physical properties of the oral hygiene composition. By altering this physical property, the element or resistive agent involved promotes adherence to the treatment site within the oral cavity, such as teeth, gums, or other areas. Resistive elements suitable for use within the oral hygiene composition include known agents such as silicon dioxide, fumed silica, silica gels, hyroxyethylcellulose, lanolate, and other fatty acids. U.S. Pat. No. 6,254,388 (Yarborough) describes the uses of such resistive agents for protection in a dental bleaching substance. Sodium Silicate is beneficial due to its affinity for iron and other heavy metals that tend to degrade the effectiveness of the photosensitive agent in the oral hygiene composition. Iron and other heavy metals occur within blood serum in the oral cavity and degrade the effectiveness of the photosensitive agent in targeting and destroying harmful bacteria. Resistive elements in the oral hygiene composition also protect the photosensitive agent from the degrading effects of enzymatic action of saliva. Sodium silicate and other resistive elements protect the photosensitive agent from these naturally occurring substances for sufficient time to allow for effective treatment. The present invention includes an oral hygiene composition well suited for use in the oral cavity due to its resistance to any decomposition and its qualities making it ideal for adherence to plaque and the teeth. All of the above-listed resistive elements increase the viscosity of the oral hygiene composition, promoting adherence to teeth or other treatment sites within the oral cavity. Chemical and physical protection of the photosensitive agent within the oral hygiene composition promotes effective destruction of harmful bacteria.

Figure 2:
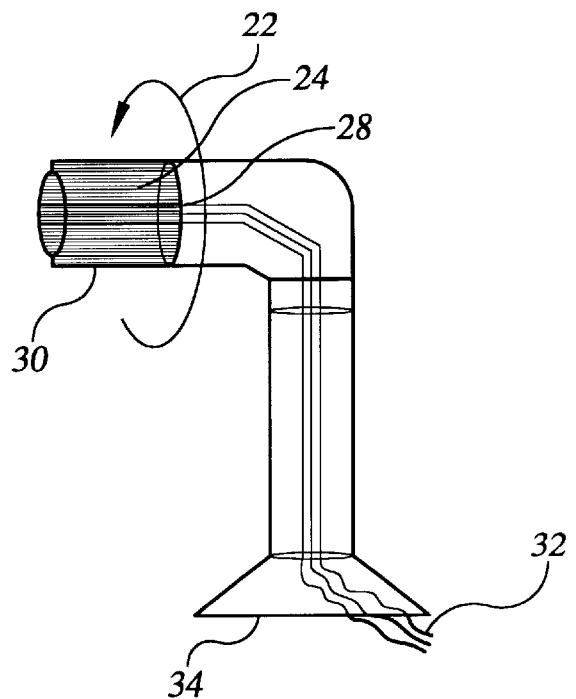
FIG. 2 is a view of the end of the dental device showing a diode or lamp as a light source rather than a laser.

In another preferred embodiment, shown in FIG. 2, the oral hygiene composition and dental device are similar to those described in FIG. 1. A laser is the light source in this embodiment. The water source transports the laser to the oral cavity through the toothbrush along with water or a similar liquid. The liquid jet included in the device carries the light using the total reflection method, making the laser source inherently safe. The bristles of the device can also act as fiberoptic transmitters. The longer bristles, acting as fiberoptics, assist in activating the photosensitive agent in the interdental spaces as well. The oral cavity is cleaned in a procedure similar to that laid out in the preceding paragraph.

Figure 3:
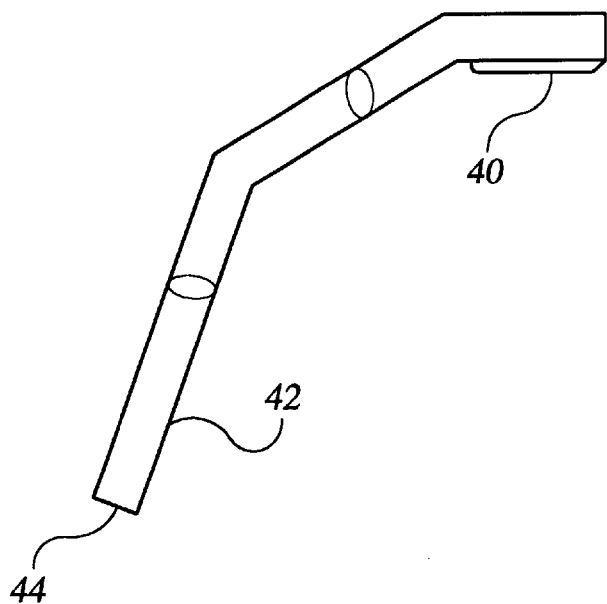
FIG. 3 is a view of an alternative light-providing device utilizing a light emitting diode or lamp as a light source.

In another preferred embodiment, shown in FIG. 3, the photosensitive agent is activated by way of a slightly different dental device; again, a diode, lamp, laser, or other light source may be used. The absorption spectrum of Hypericin or other suitable photosensitive agents easily absorbs light in the visible spectrum. The oral hygiene composition is taken into the mouth and gargled, applied via a conventional toothbrush, or applied by other means. The light source is applied throughout the mouth, activating the photosensitive agent and allowing it to destroy harmful bacteria. The light is of suitable size to allow for safe and easy maneuvering within the oral cavity, and the body of the light source is jointed or pliable to allow for access to difficult spaces or angles within the mouth. The oral hygiene composition can then be brushed and washed away similar to a conventional tooth cleaning method.

Hypericin, a clinically approved compound, is a photosensitive agent used for treatment of depression and experimentally on AIDS and cancer-related illnesses. U.S. Pat. No. 6,001,882 (Fox et al) describes the various uses for Hypericin. Overexposure to hypericin results in hypersensitivity to sunlight—a common side effect in AIDS and cancer test groups using the drug. The test groups experienced rashes and other skin ailments that are related to the hypersensitivity. In the embodiments of the present invention, Hypericin needs only to be delivered in sufficiently low doses as to avoid any potential adverse reaction. Hypericin is a preferred photosensitive agent because it has a broad absorption spectrum, making it ideal for use with a wide range of visible light sources. In its present formulation, Hypericin and other photosensitive agents are part of a self- or professional care system. Hypericin's broad absorption spectrum makes it an ideal candidate for use with an array of light sources in a preventative, home care system. In addition, the ability of an oral hygiene composition to selectively target harmful bacteria and positively alter the microbial balance of the mouth point to a primarily prophylactic use. However, the present invention may also be used in targeting and curing lesions and other medical problems that already exist in the oral cavity—activities ideally performed by a medical professional.

Hypericin and other photo-pharmaceuticals can be conjoined with other compounds that form a targeting mechanism, allowing the oral hygiene composition to positively alter the microbial balance of the mouth. There are microbes existing in the oral cavity that are of benefit to humans. The oral hygiene composition targets and destroys only harmful bacteria. FIG. 4 shows hypericin's relative constancy of absorption in the visible range. This characteristic increases absorption from visible light sources described in the embodiments.

Antibodies are any number of protein molecules produced by b-cells as a primary immune defense. They are proven effective at targeting bacteria in the oral cavity. U.S. Pat. No. 6,251,419 (Graber et al) describes the advantages of using antibodies to regenerate gums and other oral tissue lost as a result of periodontitis. The ability of antibodies to target harmful bacteria makes it suitable for use as a vector molecule in the present invention.

Other substances well suited for use as a vector molecule are polylysine residues. Polylysine is a polymer that can act as a targeting drug carrier. It couples with the photopharmaceutical to allow for more specific targeting of harmful bacteria in the oral cavity. U.S. Pat. No. 6,262,030 (Wu et al) describes the use of polylysine to couple with various pharmaceuticals to target harmful diseases in the body cavity. Its targeting characteristics are suitable for use in the present invention.

The present invention is further illustrated by the following examples, but is not limited thereby.

EXAMPLE #1

A dental device is employed in accordance with FIG. 1. Source 20 provides electrical power. Source 18 provides water or other liquids, and the oral hygiene composition. Rinse may also be applied directly to the rotating brush-head 10. A diode, lamp, or other light source emits from outlet 14. The water, oral hygiene composition, and light source emit from the device at outlet 14, between bristles 12 or in the middle of circular brush head 10. After application of the oral hygiene composition and a proper period of time to allow for targeting of harmful bacteria, the user activates light source 14. Longer bristles 16 on rotating brush-head 10 extend beyond standard bristles 12 to remove plaque and photosensitive agent from inter-dental and other hard to reach spaces. Water from source 18 may be applied to rinse away residue at the close of the procedure. Brush head 10 represents a removable and replaceable component in order to replace worn bristles. Power source 20 extends to an independent direct current source or plugs into a wall socket for home and traveling use. Water source 18 connects to a transportable reservoir for travel, or directly to a faucet for home or travel use, using an expandable or replaceable connector for fit. Light source 14 is an independent, replaceable component for ease of switching worn bulbs or diodes. The diode or lamp is available in different wavelengths to optimize radiation with the absorption spectrum of the photosensitizing agent. Hypericin has a wide absorption spectrum, making white light the optimal source.

EXAMPLE #2

A dental device is designed in accordance with FIG. 2. The embodiment is similar to FIG. 1, except that a laser source 32 is used in place of a lamp or diode as a radiation source. The laser transmits from outlet 28, in the middle of rotating brush-head 22, and around or adjacent to water source 32. The laser provided by source 32 is transported to the mouth by way of the water jet, using the total reflection method, or by way of a separate fiber. The separate bristles 24 may also act as fiberoptic threads that transmit the laser. The water source could also encircle the light source. Oral hygiene composition is applied in similar terms to Example 1. Laser source 32 is activated and teeth are cleaned similar to Example 1. Laser source 32, fibers and outlet 28 are independent, removable components of the device to ensure ease of replacement. Longer bristles 30 ensure adequate cleaning in the interdental spaces. In this embodiment, bristles acting as fiberoptic transmitters may also transmit radiation into the interdental spaces.

EXAMPLE #3

A dental device or light source is designed in accordance with FIG. 3. Source 44 provides power to the diode, laser, or light source 40. Plastic body 42 is pliable, has joints, or employs other means to ensure maneuverability and access to all areas of the oral cavity. Oral hygiene composition is applied by use of a conventional toothbrush or other means. Light source 40 is then activated, which initiates the photosensitive agent. User then employs a conventional toothbrush or other means to clean teeth and move away residue from teeth and the remainder of the oral cavity. The light source 40 in FIG. 3 is also removable to ensure cost-efficient replacement in the event of normal wear and tear.

Having described preferred embodiments of the invention with reference to the accompanying drawings, it is to be understood that the invention is riot limited to the precise embodiments, and that various changes and modifications may be effected therein by those skilled in the art without departing from the scope or spirit of the invention as defined in the appended claims.

What is claimed is:

1. An oral hygiene composition comprising:
 a photosensitizer, having a broad absorption spectrum at visible wavelengths, said photosensitizer being safe for consumption in modest quantities;

a compound for protecting the photosensitizer from harmful effects of blood serum, saliva, or other bodily fluids in the oral cavity; and wherein said photosensitizer is conjoined with vector molecular fragments to form a targeting mechanism that can selectively reduce harmful bacteria in the oral cavity.

2. The oral hygiene composition according to claim 1, wherein said vector molecular fragments are poly-lysine residues.

3. The oral hygiene composition according to claim 1, wherein said oral hygiene composition adheres well to affected areas of the oral cavity, allows attachment of said photosensitizer to desired locations, and has sufficient resistive characteristic to the decomposing effects of saliva and other natural bodily defenses.

4. The oral hygiene composition according to claim 1, wherein said photosensitizer is selected from the group consisting of an extract of St. John's wart, hypericin and erythrosine B.

5. A method for oral hygiene comprising the steps of:

a. applying a oral hygiene composition as claimed in claim 1, to surfaces within a user's oral cavity;

b. activating said oral hygiene composition with a dental hygiene device comprising at least one light source, having emission wavelength characteristics which overlap the absorption characteristics of said oral hygiene composition of claim 1, wherein said at least one light source having power output matching requirements for activating said oral hygiene composition of claim 1, and means to transmit light from said at least one light source to said oral hygiene composition within a user's oral cavity; and c. rinsing any residue from said user's oral cavity.

* * * * *